(12) United States Patent
Kopf-Sill et al.

(10) Patent No.: US 6,511,853 B1
(45) Date of Patent: Jan. 28, 2003

(54) OPTIMIZED HIGH-THROUGHPUT ANALYTICAL SYSTEM

(75) Inventors: Anne R. Kopf-Sill, Portola Valley, CA (US); Andrea W. Chow, Los Altos, CA (US)

(73) Assignee: Caliper Technologies Corp., Mountain View, CA (US)

( * ) Notice: Subject to any disclaimer, the term of this patent is extended or adjusted under 35 U.S.C. 154(b) by 229 days.

(21) Appl. No.: 09/630,866

(22) Filed: Aug. 2, 2000

Related U.S. Application Data

(62) Division of application No. 09/233,700, filed on Jan. 19, 1999, now Pat. No. 6,150,119.

(51) Int. Cl.⁷ .................... G01N 33/558; G01N 33/53; C12Q 1/68
(52) U.S. Cl. .................. 436/514; 436/514; 436/517; 435/7.1; 435/7.2; 422/68.7; 422/81; 422/82; 422/100; 204/403.01
(58) Field of Search ............................... 366/341, 336; 422/50, 68.1, 81, 82; 435/4, 6, 7.1, 7.2; 436/501, 514, 517; 204/400, 403.01

(56) References Cited

U.S. PATENT DOCUMENTS

| | | |
|---|---|---|
| 4,390,403 A | 6/1983 | Batchelder |
| 4,908,112 A | 3/1990 | Pace |
| 5,126,022 A | 6/1992 | Soane et al. |
| 5,180,480 A | 1/1993 | Manz |
| 5,498,392 A | 3/1996 | Wilding et al. |
| 5,571,410 A | 11/1996 | Swedberg et al. |
| 5,585,069 A | 12/1996 | Zanzucchi et al. |
| 5,593,838 A | 1/1997 | Zanzucchi et al. |
| 5,599,432 A | 2/1997 | Manz et al. |
| 5,603,351 A | 2/1997 | Cherukuri et al. |
| 5,635,358 A | 6/1997 | Wilding et al. |
| 5,637,469 A | 6/1997 | Wilding et al. |
| 5,699,157 A | 12/1997 | Parce |
| 5,750,015 A | 5/1998 | Soane et al. |
| 5,779,868 A | 7/1998 | Parce et al. |
| 5,800,690 A | 9/1998 | Chow et al. |
| 5,842,787 A | 12/1998 | Kopf-Sill et al. |
| 5,852,495 A | 12/1998 | Parce |
| 5,869,004 A | 2/1999 | Parce et al. |
| 5,876,675 A | 3/1999 | Kennedy |
| 5,880,071 A | 3/1999 | Parce et al. |
| 5,882,465 A | 3/1999 | McReynolds |
| 5,942,443 A | 8/1999 | Parce et al. |
| 5,957,579 A | 9/1999 | Kopf-Sill et al. |
| 6,001,229 A | 12/1999 | Ramsey |
| 6,046,056 A | 4/2000 | Parce et al. |

FOREIGN PATENT DOCUMENTS

| | | |
|---|---|---|
| WO | WO9604547 | 2/1996 |
| WO | WO9702357 | 1/1997 |

OTHER PUBLICATIONS

Dasgupta, P.K. et al., "Electroosmosis: A Reliable Fluid Propulsion System for Flow Injection Analysis," *Anal. Chem.* 66:1792–1798 (1994).
Jacobson, S.C. et al., "Fused Quartz Substrates for Microchip Electrophoresis," *Anal. Chem.* 67:2059–2063 (1995).
Manz, A. et al., "Electroosmotic pumping and electrophoretic separations for miniaturized chemical analysis systems," *J. Micromech. Microeng.* 4:257–265 (1994).
Ramsey, J.M. et al., "Microfabricated chemical measurement systems," *Nature Med.* 1:1093–1096 (1995).
Seiler, K. et al., "Planar Glass Chips for Capillary Electrophoresis: Repetitive Sample Injection, Quantitation, and Separation Efficiency," *Anal. Chem.* 65:1481–1488 (1993).
Seiler, K. et al., "Electroosmotic Pumping and Valveless Control of Fluid Flow Within a Manifold of Capillaries on a Glass Chip," *Anal. Chem.* 66:3485–3491 (1994).

*Primary Examiner*—Andrew Wang
*Assistant Examiner*—My-Chau T. Tran
(74) *Attorney, Agent, or Firm*—Matthew B. Murphy; Andrew L. Filler

(57) ABSTRACT

Throughput rates for microfluidic serial analysis systems are optimized by maximizing the proximity and speed with which multiple different samples may be serially introduced into a microfluidic channel network. Devices are included that include optimized parameters based upon desired throughput rates for a given set of reagents, reaction times and the like.

15 Claims, 6 Drawing Sheets

OPTIMIZED HIGH-THROUGHPUT ANALYTICAL SYSTEM

CROSS-REFERENCE TO RELATED APPLICATION

This application is a division of U.S. patent application Ser. No. 09/233,700, filed Jan. 19, 1999, now U.S. Pat. No. 6,150,119.

BACKGROUND OF THE INVENTION

Microfluidic analytical systems are being looked to more and more as a viable means for meeting to the desire to increase throughput, decrease costs, improve automation, and improve data quality in the analysis of chemical and biochemical systems. In many cases, the promise of microfluidics to accomplish many of these goals has been met through the massive parallelization of miniaturized conventional technologies. While providing many benefits over the conventional technologies, the simpler massively parallel systems result in only incremental improvements over conventional technologies, e.g., by a factor of the number of parallel channels. In particular, while removing some of the limitations of conventional technologies, these simpler microfluidic systems do not remove them all. Thus, these systems typically make a minor improvement over conventional systems, e.g., costs, only to run into a further limitation that the microfluidic system doesn't solve, e.g., concurrent control of parallel systems.

Commonly owned Published International Application No. 98/00231 describes methods and systems that address some of these concerns. In particular, assay methods are described that screen test compounds, e.g., pharmaceutical library compounds, in series to determine whether any of these compounds have a desired effect on a given biological system. By screening the compounds in series in a single microfluidic channel network, control of the system is simplified, while still yielding the relatively high serial throughput. Additionally, the throughput is further increased when the system is parallelized, e.g., by providing multiple separate channel networks in which multiple compounds are serially screened.

In serialized systems, however, difficulties can arise in attempting to maximize throughput. In particular, optimizing throughput requires minimizing space between serially introduced compounds within the system. However, a number of factors, e.g., diffusion, electrophoretic biasing, dispersion of fluid materials, etc., weigh against the minimization of the space between adjacent serially introduced compounds. In particular, because fluid samples will diffuse, disperse, and be electrophoretically biased, or smeared, it has typically required that substantial space be given to each fluid volume, in order to avoid intermixing of fluid materials that are introduced in succession. The more space that is required between test compounds, the more time it will take to screen multiple compounds. Further, such dispersion can result in excessive dilution of fluid materials within microscale channels. Due to the extremely small dimensions of microfluidic systems, one generally begins a microfluidic analysis with substantially less material than in conventional analyses, one often cannot afford to have such a dilution occur.

Despite this, it would generally be desirable to provide microfluidic systems, methods of using these systems and methods of designing these systems, which systems are capable of maximizing throughput by permitting materials to be introduced serially, with a minimum amount of space between them. The present invention meets these and a variety of other needs.

SUMMARY OF THE INVENTION

The present invention generally provides methods, devices and systems having optimized throughput rates for serially processed materials in microfluidic channel systems.

For example, in a first aspect, the present invention provides methods of serially transporting a plurality of test compound plugs in a microfluidic channel. The method comprises providing a first microfluidic channel having a smallest cross sectional dimension that is less than a maximum dimension d, where:

$$d = \frac{P}{n}\sqrt{\frac{D}{2KT}};$$

A first test compound plug is introduced, followed by an adjacent spacer fluid plug, where P is the period of time used to introduce the test compound plug and the adjacent spacer fluid plug into the channel. D is the diffusion coefficient of the test compound in the test compound plug. T is an amount of time for the test compound plug to move from introduction into the channel to a point of detection. K is a proportionality constant based upon the nature of the channel's cross sectional shape. n is a ratio of initial plug length to average dispersion distance for the test compound in the test compound plug in time T, provided that T is greater than P. A second test compound plug is then introduced adjacent to the spacer fluid plug.

Another aspect of the present invention is a microfluidic device, comprising a body structure which has at least a first microfluidic channel disposed within it. The channel has a smallest cross-sectional dimension of less than d, wherein:

$$d = \frac{\frac{L_p}{n} - \sqrt{2DT}}{U\sqrt{\frac{2KT}{D}}}$$

First and second test compound plugs are disposed in the channel separated by a spacer fluid plug. The first test compound plug and spacer fluid plug have a length of $L_p$, n is a ratio of initial plug length to desired dispersion distance of the test compound in the test compound plug, and is between about 0.5 and about 10, D is a diffusion coefficient of the first test compound. T is an amount of time for the test compound plug to move from introduction into the channel to a point of detection. U is an average linear velocity of the test compound plug through the first microscale channel. K is the proportionality constant based upon the nature of the channel's cross-sectional shape.

A further aspect of the present invention is a method of designing a microfluidic channel network for performing a serial analysis. The method comprises selecting a cycle length of a test plug containing a test compound plug and a spacer plug. A diffusion coefficient of the test compound is identified. A total reaction time is selected for the test compound. One or more of a maximum channel diameter and a channel length for carrying out the analysis is determined, based upon the cycle length, diffusion coefficient and total reaction time. The test compound in the test compound plug disperses across less than 50% of the spacer fluid plug during the total reaction time.

BRIEF DESCRIPTION OF THE FIGURES

FIG. 5A schematically illustrates a cross-section of a rectangular channel, while

DETAILED DESCRIPTION OF THE INVENTION

I. General Discussion

The present invention provides methods of performing high-throughput and even ultra-high-throughput experimentation in microfluidic devices and systems by minimizing the amount of time required between samples that are serially passing through the channels of the device or system. In particular, the present invention provides methods of maximizing throughput of serially introduced, but spaced apart fluid samples in microfluidic channels by providing a microfluidic channel that meets a number of optimal criteria. In general, by providing the microfluidic systems of sufficiently small cross-sectional dimensions, and by applying fluid manipulation that operates in the laminar flow range, one can substantially reduce the level of diffusion, dispersion, and other perturbing effects in microfluidic channels, and thereby minimize the amount of space between serially introduced materials. By reducing the amount of space between these serially introduce materials, one can maximize the number of different materials that can be serially introduced into the channel per unit time, also termed "throughput." Compounds that are screened at rates greater than 1 compound/minute within a single channel are generally termed high-throughput, while screening of compounds at a rate greater than 1 compound/10 seconds generally fall into the ultra-high throughput category.

Figure 1:
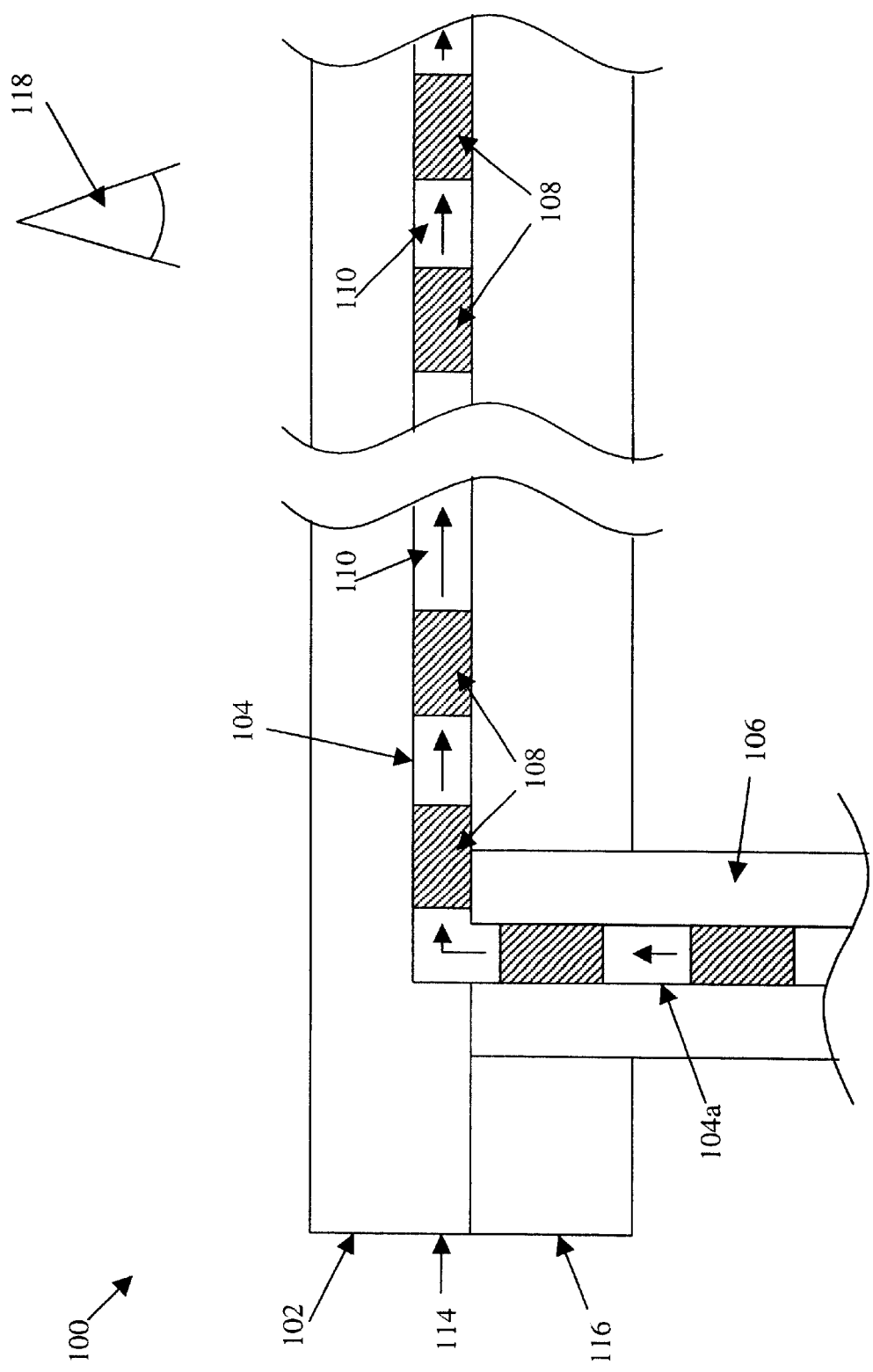
FIG. 1 schematically illustrates an example of a microfluidic system for performing serial analyses on a plurality of sample material/test compound plugs, in cross section.

FIG. 1 schematically illustrates the serial analysis methods and systems of the present invention. As shown, a microfluidic device 100 includes a body structure 102, having disposed therein a main analytical channel 104. The main analytical channel 104 is typically in fluid communication with sources (not shown) of the various sample materials/test compounds that are to be serially analyzed in the main channel 104. As shown, communication of the main channel with the sources of sample material is provided through an integrated pipettor element 106 that includes a channel 104a disposed through it, where channel 104a is in fluid communication with the main analytical channel 104. In operation, reagents for a given analysis are typically flowed along the main channel 104. The plurality of sample material/test compound plugs 108 are then serially introduced into the main channel where they interact with the analysis reagents. Spacer fluid plugs 110 are introduced into the pipettor channel 104a and analytical channel 104, in order to maintain separation between consecutively introduced test plugs. The test plugs and interacting reagents are transported along main channel 104 (as shown by the arrows), until they reach a detection point in the channel which is in sensory communication with a detector, e.g., optical detector 118. As is clear from FIG. 1, the closer that one is able to pack test plugs together in the channels of the system, the more test plugs one can analyze per unit time. This aspect of serial high-throughput analyses is directly addressed by the methods and systems of the present invention.

In particular, the present invention provides a method of transporting at least two different fluid regions through a microfluidic channel whereby dispersion or diffusion of the two fluid regions into each other is minimized. In accordance with the present invention, this is generally accomplished by providing the microfluidic channel, which has the dimensions of the channel optimized for throughput and minimal dispersion/diffusion of test plug materials. This is generally accomplished by selecting an optimal channel cross-sectional dimension for a given analytical system, e.g., reaction time, diffusion coefficient of test plug materials, desired stringency/resolution of test plugs, and the like. As discussed herein, "dispersion" is defined as convection-induced, longitudinal dispersion of material within a fluid medium due to velocity variations across streamlines, e.g., in pressure driven flow systems, electrokinetically driven flow systems around curves and corners, and electrokinetically driven flow systems having non-uniform buffer ionic concentrations, e.g., plugs of high and low salt solutions within the same channel system. For the purposes of the channel systems of the present invention, dispersion is generally defined as that due to the coupling between flow and molecular diffusion, i.e., Taylor dispersion. In this regime, the time-scale for dispersion due to convective transport is long or comparable to the time scale for molecular diffusion in the direction orthogonal to the flow direction. For discussions on dispersion and Taylor dispersion in particular, see, e.g., Taylor et al., Proc. Roy. Soc. London, (1953) 219A:186–203, Aris, Proc. Roy. Soc. London (1956) A235:67–77, Chatwin et al., J. Fluid mech. (1982) 120:347–358, Doshi et al., Chem. Eng. Sci. (1978) 33:795–804, and Guell et al., Chem. Eng. Comm. (1987) 58:231–244, each of which is incorporated herein by reference in its entirety for all purposes.

II. Optimized Microfluidic Systems

Figure 2:
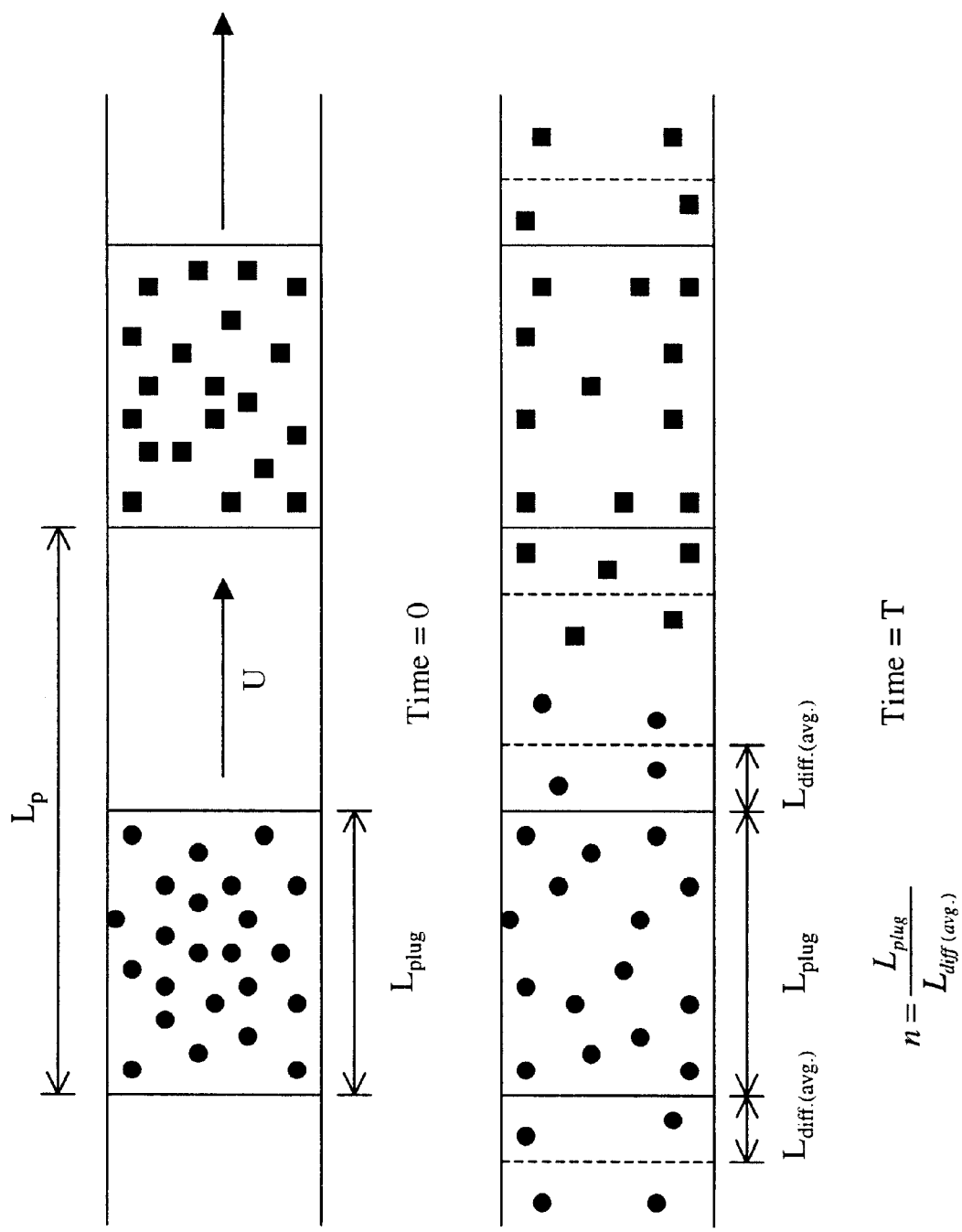
FIG. 2 schematically illustrates the diffusion/dispersion of sample materials/test compound materials during a particular analysis within a microfluidic channel of a microfluidic device.

Diffusion/dispersion of test plug materials within a microfluidic channel is schematically illustrated in FIG. 2. In particular, test plugs are illustrated as clean, non-diffuse plugs at the point of initial introduction into the channel (Top panel, time=0). After a given time (T) during which the test plugs are transported along the channel, the materials within the test plugs, illustrated as circles and squares, diffuse and disperse out of the original test plug volumes, as shown in FIG. 2 (Bottom panel). The average dispersion distance is illustrated by the dashed lines. The original test plug length ($L_{plug}$), the period length ($L_p$) and the linear velocity (U, arrows) are illustrated within the FIG. 2, as is the correlation of the desired dispersion distance to n, which is described in greater detail below. As described herein, optimized microfluidic channels are selected/designed which do not permit excessive diffusion/dispersion, e.g., beyond a desired level of diffusion/dispersion, e.g., as shown by the dashed lines.

Identifying the optimal criteria for the microfluidic channel systems used in accordance with the present invention involves the consideration of many factors. For example, one must consider both the structural characteristics of the system, as well as the temporal and chemical demands of the particular application for which the system is to be used in order to optimize the system.

In particular, in determining how close together fluid plugs of a given sample or test compound material, also referred to as "test plugs," may be introduced into a channel, one must consider: (1) properties of the material, such as the diffusion coefficient of the material; (2) requirements of the application, such as the amount of time required between introduction of the sample or test compound material and detection of that material, e.g., to produce a sufficient detectable signal, and the acceptable level of material plug cohesiveness; and (3) the structural properties of the microfluidic channel, such as the cross sectional dimensions of the channel. Of course, a number of other considerations can also influence each of the above criteria, including, e.g., cost of manufacturing microfluidic devices and systems, reaction speeds, sensitivity of detection schemes, and the like. However, the present invention provides methods of producing and using microfluidic devices and systems, which are optimized for the above-described criteria, while also permitting the optimization of these latter criteria and other influential factors.

As noted, optimizing throughput of a particular serial input system for performing a given assay typically requires serially introducing test plugs as close together as possible, without having excessive intermixing of adjacent test plugs. As a first order, this requires the introduction of spacer fluid plugs between the test plugs, in order to provide the separation between test plugs. As a second order, however, the length of the spacer plug is taken into consideration, and minimized in order to maximize the number of test plugs moved through the system per unit time, while still performing the requisite separation or partitioning function. This minimization of the spacer fluid plug requires consideration of the rate at which the materials in the test plug will diffuse or disperse while traveling through the microfluidic channel, and selection of a spacer fluid plug length that allows only an acceptable level of diffusion/dispersion.

Dispersion of a test plug material is analogous to diffusion of that material. Thus, the dispersion coefficient E is analogous to the diffusion coefficient of the material, and is defined as follows:

$$E = K\frac{d^2 U^2}{D} \qquad (1)$$

where d is the smallest cross sectional dimension of the channel, U is the average linear velocity of material moving through the channel in mm/sec, K is the proportionality factor which is a functional of the channel's cross-sectional shape, and D is the molecular diffusion coefficient of the material or solute. The distance that a molecule diffuses (x) is given by the following equation:

$$x = \sqrt{2DT} \qquad (2)$$

where T is the amount of time over which diffusion is determined. Given that both dispersion and diffusion are present in a particular system, one can then treat dispersion as an additional diffusion source, and calculate the distance that a molecule travels, through the combination of diffusion and dispersion as follows:

$$x = \sqrt{2K\frac{(dU)^2 T}{D} + \sqrt{2DT}} \qquad (3)$$

As described previously, the true area of concern with relation to the systems described herein is the distance that a given molecule moves relative to the length of a combined test/spacer plug, $L_p$. Defining the ratio of the plug length to the diffusion distance as n, one obtains the following equation where:

$$\frac{1}{n} = \frac{x}{L_p} = \frac{\sqrt{2K\frac{(dU)^2 T}{D}} + \sqrt{2DT}}{L_p} \qquad (4)$$

Rearranging this equation to solve for d, one then obtains the equation:

$$d = \frac{\frac{L_p}{n} - \sqrt{2DT}}{U\sqrt{\frac{2KT}{D}}} \qquad (5)$$

where d is the upper limit on the diameter of the channel in question, under a particular set of parameters, e.g., test/spacer plug length $L_p$, linear velocity of the material in the channel U, retention time in the channel T, and desired or acceptable dispersion distance n.

If the time required to introduce a single cycle of test plug and spacer is defined as P, which is the inverse of the throughput of the system, then the original period length $L_p$, can be rewritten as the product of the linear velocity of the test plug/spacer fluid plug, U, and the time period for introducing these plugs, P. This then simplifies the above equation as follows:

$$d = \frac{P}{n}\sqrt{\frac{D}{2KT}} - \frac{1}{U}\sqrt{\frac{D^2}{K}} \qquad (6)$$

Typically, in microfluidic systems, the effect of molecular diffusion is only important in cases where diffusion is relatively fast, while the linear velocity of the system is slow, e.g., where D is large and U is small. However, in typical microfluidic systems the inverse is generally true, as one is generally desirous of moving materials through the system before they have the opportunity to diffuse excessively. As such, the second term in the above equation becomes negligible and can generally be ignored, thus leaving the equation:

$$d = \frac{P}{n}\sqrt{\frac{D}{2KT}} \qquad (7)$$

Based upon the above equation, one can optimize a serial input, high throughput analysis by merely plugging in those parameters that are defined by the particular assay, and adjusting or optimizing those parameters that are not given. For example, given a desired retention time (T) within a channel for a test compound having a given diffusion coefficient (D), a desired resolution between compounds (n), and a desired throughput rate (1/P), one can then determine the maximal smallest cross-sectional dimension for the channel (d) in which the analysis is to be carried out. Conversely, given a particularly dimensioned channel (d), one can identify the maximum analysis time (T) permitted for a given test compound having a particular diffusion coefficient (D) and a desired resolution between compounds (n). The various parameters are also illustrated in FIG. 2, e.g., where n is illustrated as being the ratio of the starting length of the test plug ($L_{plug}$), to the average diffusion length of the test compound material at time T ($L_{diff(avg.)}$). As shown in FIG. 2, the dashed line represents that average dispersion or diffusion distance of the test compound material at time T.

Accordingly, in a first aspect, the present invention provides a method of serially transporting fluid plugs that contain sample material or test compound material (referred to herein as "test plugs") through a microfluidic channel, where those test plugs are separated by plugs of spacer fluid, e.g., buffer. In order to accomplish this, the microfluidic channel through which the test plugs are serially transported is provided having its smallest cross-sectional dimension that is less than or equal to about d where:

$$d = \frac{P}{n}\sqrt{\frac{D}{2KT}}$$

and wherein D is the diffusion coefficient of the sample material or test compound material in the test plug in the fluids present, T is the total retention time of the test plug in the microfluidic channel, e.g., from introduction of the test plug into the channel to detection of a given result from the test plug at some point along the channel. In particularly preferred aspects, P is less than about 60 seconds, D is between about $10^{-5}$ and about $10^{-8}$ cm$^2$/s, T is greater than 1 second, and n is between about 0.5 and about 20.

In a related aspect, the present invention provides a microfluidic devices for performing serial high-throughput analyses. In particular, these devices typically include a body structure that comprises at least a first microfluidic channel disposed therein. At least one of the channels has a smallest cross-sectional dimension of less than d, wherein:

$$d = \frac{\frac{L_p}{n} - \sqrt{2DT}}{U\sqrt{\frac{2KT}{D}}} \quad (8)$$

first and second test compound plugs disposed in the channel separated by a spacer fluid plug, wherein the first test compound plug and any optionally included spacer fluid plug have a length of $L_p$, n is a ratio of initial plug length to desired dispersion distance of the test compound in the test compound plug, and is between about 0.5 and about 10, D is a diffusion coefficient of the first test compound, K is a proportionality factor, T is an amount of time for the test compound plug to move from introduction into the channel to a point of detection, and U is an average linear velocity of the test compound plug through the first microscale channel. In particularly preferred aspects, $L_p$ is less than about 10 mm, preferably less than or equal to about 6 mm, U is between about 0.05 and about 10 mm/sec and preferably between about 0.2 and 2 mm/sec, D is between about $10^{-5}$ and about $10^{-8}$ cm$^2$/s, T is greater than about 1 second, K is greater than about 1/210, and preferably between about 1/210 and 1/24, and n is between about 0.5 and about 10.

Figure 5B:
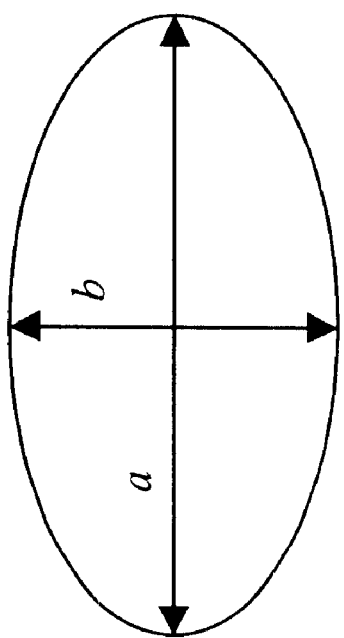
FIG. 5B illustrates a cross-section of an elliptical channel with the major and minor axes labeled appropriately.

As noted above, the nature of dispersion in microchannels is dependent, at least in part, on the cross-sectional shape of the microchannel in question. For example, channels that are cylindrical, e.g., having a circular cross-sectional shape have a different dispersion profile than for channels that are elliptical, rectangular of finite width or infinite width, i.e. are not limited by the width. The above-described calculations are still applicable to these different channel geometries through the incorporation of the proportionality factor K in each case. In the case of cylindrical channels, this proportionality constant is 1/192. For elliptical channels, on the other hand, the proportionality constant (K) is given by the following equation:

$$K = \frac{1}{192}\left(\frac{5 + 14r^2 + 5r^4}{12(r + r^3)}\right) \quad (9)$$

when $d^2$ as used in Eq. (1), is equal to (ab) where a is the major axis of the elliptical channel and b is the minor axis of the elliptical channel (as shown in FIG. 5B), and r=b/a. Thus, in adjusting above equations (7) and (8) for elliptical channels, d would be equal to $\sqrt{ab}$.

Figure 4:
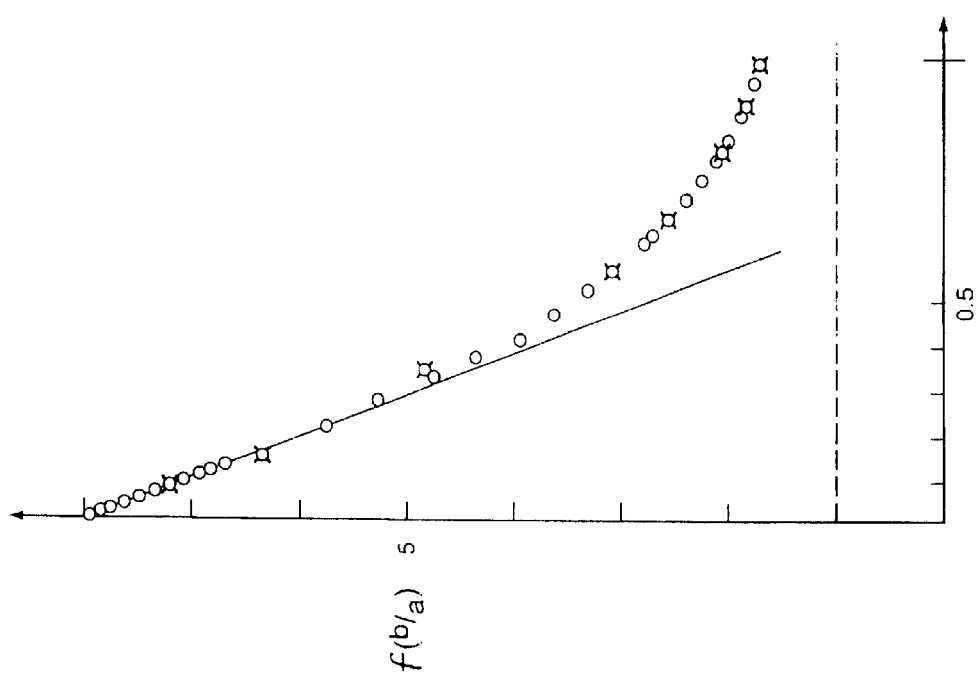
FIG. 4 is a graph which illustrates the variation of f(b/a) for laminar flow through a channel of rectangular cross-section.
Figure 5A:
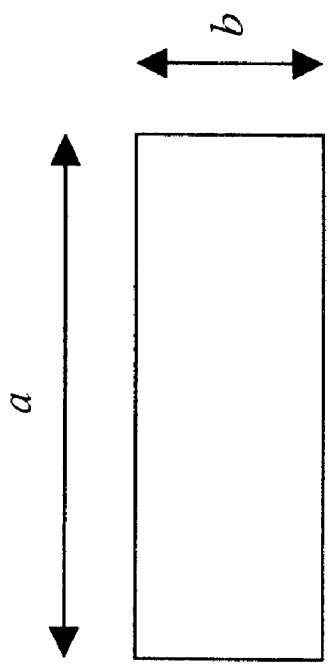

For rectangular channels where dispersion is not limited by the channel width, e.g., having an "infinite width," and where d is the channel depth, the proportionality factor is 1/210. However, for channels whose width does affect dispersion, i.e. "finite width," e.g., as shown in cross-section in FIG. 5A, the proportionality factor is as follows:

$$K = \frac{1}{210}f\left(\frac{b}{a}\right) \quad (10)$$

when f(b/a) is determined from the graph shown in FIG. 4, which was obtained from Chatwin, et al., J. Fluid Mech. (1982) 120:347–358, which is incorporated herein by reference for all purposes.

Figure 6B:
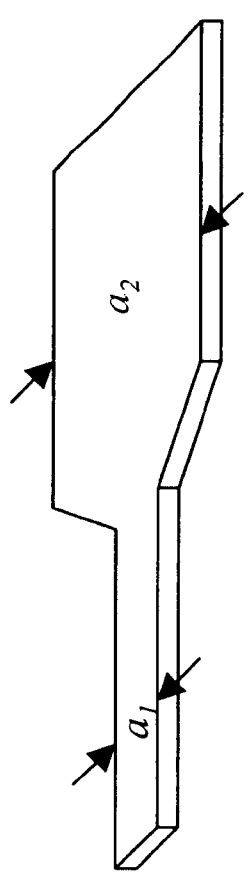
FIGS. 6A–6C schematically illustrates channels which vary in there cross sectional dimensions.
Figure 6C:
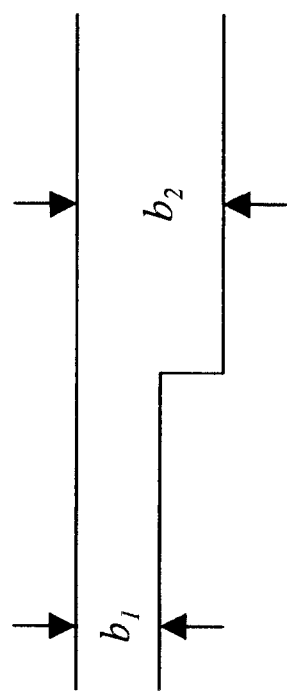
Figure 6A:
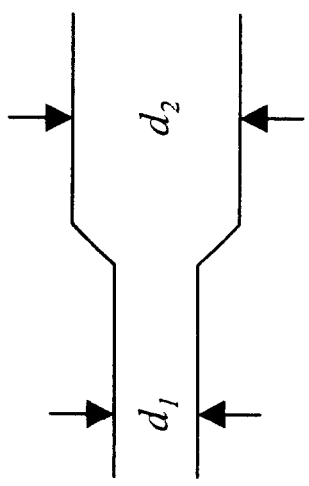

Although generally described in terms of channels with uniform cross-sectional dimensions, they are also applicable to channel systems, which include varied cross-sectional dimensions, e.g., channels that go from a narrow cross-section to a wider cross section. As schematically illustrated in FIGS. 6A–6C. In particular, the dispersion calculations described above are reformulated in terms of the constant volumetric flow rate, rather than linear velocity, as used above. Specifically, within such varying channel systems, linear velocity of fluid changes as the fluid flows from a narrow channel into a wider channel, however, the volumetric flow rate remains the same. Linear velocity is related to volumetric flow rate as follows:

$$U = \frac{Q}{S} \quad (11)$$

where S is the cross sectional area of the channel. Thus, substituting this into equation (11), above, one obtains:

$$E = K\frac{d^2Q^2}{S^2D} \quad (12)$$

Thus, in the case of a cylindrical channel, where K=1/192, the dispersion coefficient is calculated as follows:

$$E = \frac{1}{12\pi^2}\frac{Q^2}{d^2D} \quad (13)$$

Where the solute flows through a channel, which varies in diameter from $d_1$ to $d_2$, as shown in FIG. 6A, one can solve for the ratio of dispersion coefficients which ultimately yields the following:

$$\frac{E_2}{E_1} = \left(\frac{d_1}{d_2}\right)^2 \quad (14)$$

Surprisingly, it can be seen from this equation, that in moving from a narrow channel, e.g., $d_1$, to a wide channel, e.g., $d_2$, under a constant volumetric flow rate the dispersion coefficient will actually decrease in the wider channel portion, rather than increase, as one may have initially expected. This also holds true in channels of differing cross-sectional shapes, e.g., rectangular channels varying in either width or depth dimensions, e.g., as shown in FIGS. 6B and 6C, respectively, etc. For example, in a rectangular channel which varies in width (but not in depth) from $a_1$ to $a_2$, the dispersion is calculated as:

$$\frac{E_1}{E_2} = \frac{f\left(\frac{b}{a_2}\right)}{f\left(\frac{b}{a_1}\right)} \left(\frac{a_1}{a_2}\right)^2 \qquad (15)$$

Where $$\frac{f\left(\frac{b}{a_2}\right)}{f\left(\frac{b}{a_1}\right)}$$

is on the order of 1, $$\frac{E_1}{E_2} \approx \left(\frac{a_2}{a_1}\right)^2,$$

and as can be seen once again, dispersion is decreased in a channel in which the width is increased.

The same also holds true where the channel depth is increased, 'a' remains constant while b varies from $b_1$ to $b_2$, as shown by the following:

$$E = \frac{f\left(\frac{b}{a}\right)}{210} \cdot \frac{Q^2}{a^2 D} \qquad (16)$$

As can be seen, as b increases from $b_1$ to $b_2$, f(b/a) decreases which, in turn results in a decrease in relative dispersion, e.g., $$\frac{E_1}{E_2}.$$

For discussions of channels having varied cross-sectional shapes, see also Taylor et al., Proc. Roy. Soc. London, (1953) 219A: 186–203, Aris, Proc. Roy. Soc. London (1956) A235:67–77, Chatwin et al., J. Fluid mech. (1982) 120:347–358, Doshi et al., Chem. Eng. Sci. (1978) 33:795–804, and Guell et al., Chem. Eng. Comm. (1987) 58:231–244.

The present invention has been generally described in terms of providing an optimized channel cross-sectional dimension where the other elements of the channel geometry are fungible, e.g., are easily changed. However, in certain cases, other channel dimensions are predetermined for reasons not related to, e.g., throughput. For example, where optical detection methods are used, it may be necessary to utilize a channel having a sufficiently large cross-sectional dimension to allow sufficient signal acquisition by the detector. Alternatively, a channel may require a sufficiently large cross-section to allow particulate materials to pass, e.g., cells, beads or the like, or to slow linear velocity to permit adequate incubation of reactants. In such cases, the necessary cross sectional dimension can be incorporated into the above-described equations, to optimize for throughput based upon that requirement.

Diffusion coefficients for given molecules are generally a function of the size of the molecule and the nature of the medium in which the molecule is dissolved. In any event, these coefficients are generally readily determinable from the Stokes-Einstein equation for estimating a diffusion coefficient of a solute in a low viscosity solvent, as follows:

$$D = \frac{k_\beta T}{6\pi\mu R_0} \qquad (17)$$

where $k_\beta$ is Boltzmann's constant, T is the temperature of the system, $\mu$ is the solvent viscosity and $R_0$ is the solute radius. For high viscosity solvents, the diffusion coefficient varies as $\mu^{-2/3}$, while in extremely high viscosity solvents, e.g., polymer solutions and gels, diffusion is usually independent of viscosity.

In particularly preferred aspects, the methods and systems of the present invention are used in the screening of pharmaceutical libraries, e.g., large collections of compounds with potential pharmacological activity. Typically, such library compounds comprise relatively small molecules, e.g., molecular weights less than 10,000 daltons and preferably, less than about 1000 daltons. As such, these compounds generally have comparable diffusion coefficients that are less than about $10^{-5}$ and typically between about $10^{-5}$ and $10^{-8}$. In preferred aspects, optimization of microfluidic methods and systems according to the present invention is done for compounds that have diffusion coefficients in the range of from about $10^{-5}$ to about $10^{-7}$.

The total retention time (T) for a given test plug may vary depending upon a number of criteria. Typically, the retention time depends upon the amount of time required for the particular analysis to generate sufficiently detectable signal before the test plug passes in front of the detection portion of the microfluidic channel. For most fluorogenic assays, this retention time typically varies, but is typically greater than about 1 second, preferably, greater than about 5 seconds, and is often greater than 30 seconds, and in some cases, even greater than 60 seconds. Of course, for extremely fast reactions, retention time may be minimized, or selected simply to optimize the overall processing, e.g., maximizing throughput while permitting sufficient time for the sampling system to pick up the next test plug.

As noted previously, the throughput of a particular analytical channel depends, in part, on the number of test plugs one can move through the analytical channel per unit time, or how closely together one can introduce such plugs into the channel. Accordingly, the length of the test plug and its accompanying spacer plug is dependent upon the desired throughput level, as well as the necessary size of the test plug, e.g., to ensure the presence of adequate test plug material for analysis. Accordingly, this parameter is typically variable depending upon the investigator's choice. However, in the preferred application of high-throughput pharmaceutical screening, the combined length of the test plug and its adjacent spacer fluid plug ($L_p$) is from about 0.1 to about 30 mm, and more preferably, from about 1 to about 10 mm. The period length (P) for introducing a test plug and its adjacent spacer region is likewise dependent upon the length of the plugs ($L_p$), as well as the average linear velocity (U) of the plugs being introduced. Typically, the period length will vary, but will generally be less than about 60 seconds, preferably, less than 30 seconds, optimally, less than 20 seconds, and even more preferably, less than 10 seconds and often less than 5 seconds, while the linear velocity of the fluid in the system typically varies from about 0.05 m,/sec to about 10 mm/sec, and preferably, from about 0.2 mm/sec to about 2 mm/sec.

As with many of the above-described criteria, the amount of permitted diffusion/dispersion (as measured by n) is a parameter that is determined in advance by the investigator depending upon the amount of resolution that the investigator desires between test plugs. For example, where one wishes to perform a rough screen of a given library of compounds, one can tolerate far more diffusion/dispersion than if one is performing a highly stringent analysis of a number of critical samples, such as multiple patient sample analyses. The term n is defined as the inverse of the diffusion/dispersion length, in terms of the original test plug length, e.g., at time=0. Thus, for example, assuming that a test plug molecule has an average dispersion/diffusion of one fifth the length of the original sample plug, a molecule at the edge of the original test plug would diffuse/disperse an average distance of one fifth of the original plug length. In this case, n would be equal to 5. In preferred aspects, the acceptable average dispersion/diffusion in the microfluidic systems described herein is given by an n value that is greater than 0.5, preferably, greater than or equal 1, and more preferably, greater than or equal to 2 and in many cases, greater than or equal to 4. This amounts to an average dispersion distance of less than 200% of the original test plug length, preferably, less than 100%, and more preferably, less than 50%, and in many cases, less than or equal to 25%. Typically, the value of n is less than 20, often, less than or equal to 10, and in many cases, less than or equal to 8, yielding average percent dispersions of greater or equal than 5%, often greater than or equal to 10%, and in many cases, greater than or equal to 12.5%. In preferred aspects, n typically falls between the upper and lower limits described above, e.g., between 0.5 and 20, and preferably, between 1 and 10, 4 and 10, or 1 and 8.

Based upon the preferred ranges of the above-described criteria, optimized microfluidic channels according to the present invention will have a smallest cross-sectional dimension that is less than about 200 $\mu$m, preferably, less than about 100 $\mu$m, and more preferably, less than about 50 $\mu$m, and in many cases, less than about 20 $\mu$m, and even less than about 10 $\mu$m.

As will be appreciated from the instant disclosure, by providing optimization methods for microfluidic devices, the present invention also provides methods for designing such optimized systems for performing serial analyses. In particular, these methods comprise selecting a cycle length of a test plug containing a test compound plug and a spacer plug. A diffusion coefficient of the test compound is identified. A total reaction time is selected for the test compound based upon the desired reaction time as dictated by the nature of the reaction to be carried out. One or more of a maximum channel diameter and a channel length for carrying out the analysis is determined, based upon the cycle length, diffusion coefficient and total reaction time, e.g., from the above described equations. The methods are generally used to design microfluidic systems where the test compound in the test compound plug has an average dispersion distance of less than 200% of the original test compound plug length, preferably, less than 100%, more preferably, less than 50% and often less than 25% of the original test compound plug length, during the total reaction time.

Microfluidic channels, devices and systems incorporating channels having optimized dimensions, as described herein, may incorporate any of number of structural configurations from a simple capillary tube to a more complex planar microfluidic device incorporating an integrated channel network within its interior region. In preferred aspects, the microfluidic channels in which the methods described herein are carried out are a portion of an integrated channel network in a microfluidic device. While such integrated devices may comprise an aggregate of separate parts, e.g., capillary elements, microfabricated chambers, and the like, typically, such microfluidic devices have a layered structure comprised of at least two separate planar substrates that are mated together, whereby the channel network is defined at the interface of the mated substrates, e.g., by being fabricated into a surface of one or both of the planar substrate layers. Such devices are described in detail in, e.g., U.S. patent application Ser. No. 08/845,754, filed Apr. 25, 1997, and incorporated herein by reference for all purposes. An example of a microfluidic device incorporating such a layered structure is illustrated in FIG. 1, where the main body structure 102 of the device 100 is comprised of at least two separate substrate layers 114 and 116, which are mated together to define the channel portion, e.g., channel 104, of the device 100. Substrates for use in fabricating the devices described herein are typically selected based upon their ease of microfabrication, as well as their compatibility with the conditions to which they will be subjected, e.g., extremes of salt concentration, pH, pressure, temperature, and the like. Typically, silica based substrates are preferred because of their amenability to microfabrication using, e.g., photolithographic fabrication techniques, and their general inertness to reaction/analysis conditions. Alternatively preferred are polymeric substrates which provide advantages of cost and ease of fabrication over silica-based substrates using, e.g., injection molding, embossing, stamping or other fabrication methods whereby large numbers of inexpensive disposable devices may be fabricated at a time. Examples of preferred polymeric materials and methods for fabricating microfluidic devices from these materials are described in, e.g., U.S. patent application Ser. No. 08/843,212, filed Apr. 14, 1997, and incorporated herein by reference in its entirety for all purposes.

Figure 3B:
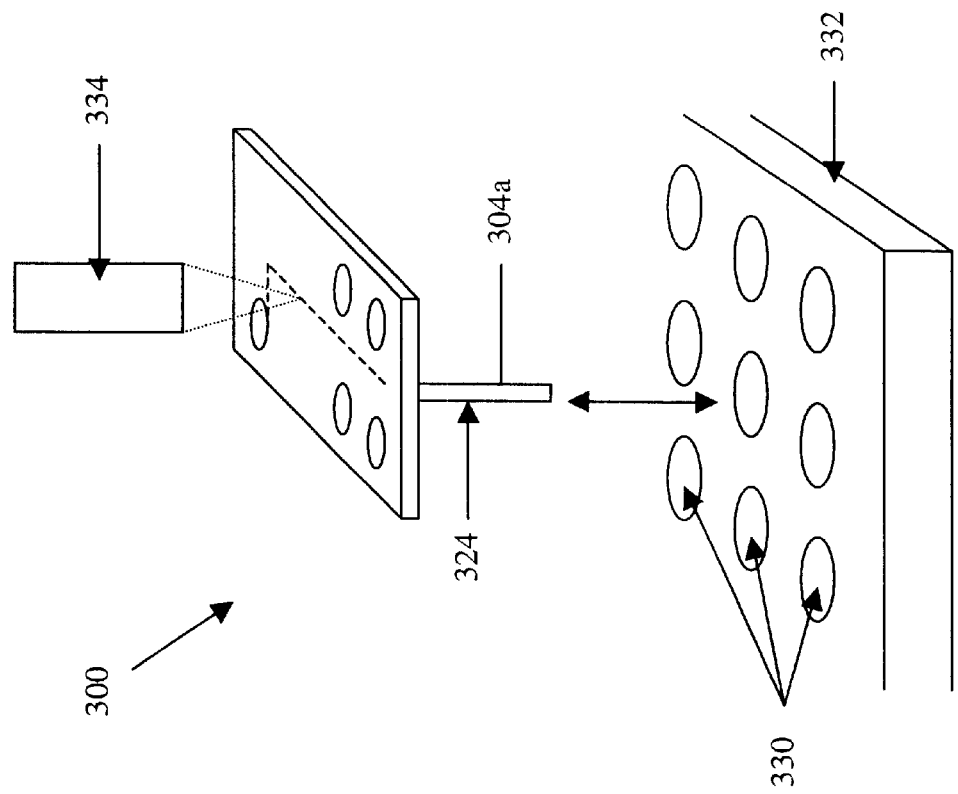
FIGS. 3A and 3B schematically illustrate a microfluidic device and system, respectively, for performing a plurality of analyses on a library of samples/test compounds that can be used in conjunction with the present invention.
Figure 3A:
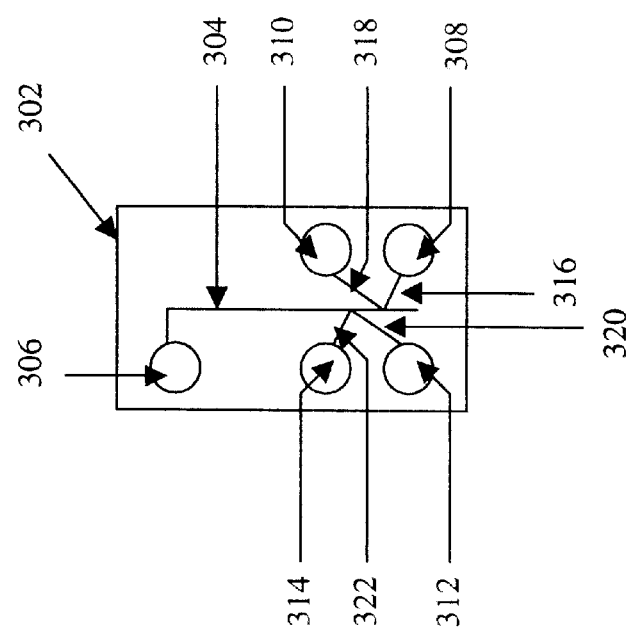

An example of a preferred overall microfluidic system 300 for use in carrying out high-throughput serial analyses is shown in FIGS. 3A and 3B. As shown, a microfluidic device 302 is provided having at least a first analytical channel 304 disposed within its interior region and which terminates at one end in a waste reservoir 306. The channel is fluidly connected to reagent sources 308–314 via channels 316–322, respectively. The analytical channel is also fluidly connected to a pipettor channel 304a disposed in pipettor element 324. Different test plugs and spacer fluid plugs are sipped into channels 304a and 304 by contacting the open end of the pipettor element 324 with the test compound sources and spacer fluid source, e.g., disposed in the wells 330 of multiwell plate 332. The test plugs, and their effect on the analysis are then detected in analytical channel 104, e.g., by detector 334.

Sipping the test fluid plugs and spacer fluid plugs into the analytical channel from he multiwell plates, as well as movement of the fluid reagents, test plugs and spacer plugs through he channels of the device shown in FIG. 3, is carried out by any of a number of methods. For example, in preferred aspects, fluid movement is carried out through the application of pressure differentials through which fluid flow is desired. This is optionally achieved by applying vacuum, e.g., negative pressures, or positive pressures to one or more of the reservoirs/ports at the termini of the various channels of the device, to controllably drive fluids through the channels. Controlled application of pressure differentials through different, intersecting channel segments allows one to control the ratio of material moving through each of the channel segments.

Alternatively, fluid transport may be provided using electrokinetic systems that move fluids and other materials through the application of electric fields along the length of those channels. The application of electric fields across channel lengths is typically achieved through electrodes placed into contact with fluids disposed in the reservoirs/ports at the various channel termini, which electrodes are coupled to an appropriate electrical controller that delivers the requisite voltages to the electrodes. By using controlled electrokinetic fluid transport systems, one can effectively control the flow and direction of fluids and other materials within the microfluidic device without the need for mechanical pumping and valving structures. Controlled electrokinetic transport is described in detail in, e.g., Published International Patent Application No. 96/04547, to Ramsey et al., which is incorporated herein by reference for all purposes.

Some exemplary analyses were set up in order to illustrate the performance of the optimization methods of the present invention. The following table illustrates a number of different criteria for different analyses, and the determination of the optimized channel cross-sectional dimension for carrying out the analysis based upon the different criteria.

TABLE 1

| D ($cm^2$/sec) | T (sec) | P (sec) | n | U (mm/sec) | Maximum d ($\mu m$) |
|---|---|---|---|---|---|
| $1 \times 10^{-5}$ | 1 | 60 | 2 | >>0.001 | 9300 |
| $1 \times 10^{-5}$ | 1 | 1 | 2 | >>0.1 | 155 |
| $1 \times 10^{-5}$ | 1 | 3 | 2 | >>0.03 | 464 |
| $1 \times 10^{-5}$ | 5 | 5 | 2 | >>0.04 | 346 |
| $1 \times 10^{-5}$ | 20 | 5 | 2 | >>0.08 | 173 |
| $1 \times 10^{-5}$ | 20 | 5 | 3 | >>0.12 | 116 |
| $1 \times 10^{-5}$ | 20 | 5 | 6 | >>0.2 | 58 |
| $1 \times 10^{-5}$ | 20 | 20 | 2 | >>0.02 | 693 |
| $1 \times 10^{-5}$ | 60 | 60 | 2 | >>0.01 | 1200 |
| $1 \times 10^{-5}$ | 60 | 60 | ½ | >>0.003 | 4800 |
| $3.3 \times 10^{-6}$ | 20 | 5 | 3 | >>0.07 | 66 |
| $3.3 \times 10^{-6}$ | 20 | 5 | 6 | >>0.013 | 33 |
| $3.3 \times 10^{-6}$ | 20 | 5 | 6 | 1.0 | 31 |
| $3.3 \times 10^{-6}$ | 20 | 20 | 3 | >0.02 | 266 |
| $3.3 \times 10^{-6}$ | 20 | 20 | 6 | >>0.03 | 66 |
| $7.0 \times 10^{-7}$ | 60 | 2 | 6 | >>0.3 | 3.5 |
| $7.0 \times 10^{-7}$ | 60 | 10 | 6 | >>0.06 | 18 |

II. Applications of Optimized Microfluidic Systems

As noted above, the optimized microfluidic channels, devices and systems of the invention are generally useful in performing high-throughput, and even ultra high-throughput serial analyses. Particularly preferred high-throughput analyses include screening large numbers of pharmaceutical library compounds for effects on biochemical systems, screening large numbers of patient samples, e.g., for clinical analysis, and the like.

The use of microfluidic devices and systems for the performance of high throughput pharmaceutical screening operations was described in detail in commonly owned International Patent Application No. WO 98/00231, which is incorporated herein by reference in its entirety for all purposes. In brief, a microfluidic channel is provided through which at least a first component of a biochemical system is flowed, typically in a continuous stream. As used herein, a "biochemical system" generally refers to a chemical interaction between molecules of the type generally found within living organisms. Such interactions include the full range of catabolic and anabolic reactions which occur in living systems including enzymatic, binding, signaling and other reactions. Further, biochemical systems, as defined herein, will also include model systems which are mimetic of a particular biochemical interaction. Examples of biochemical systems of particular interest in practicing the present invention include, e.g., receptor-ligand interactions, enzyme-substrate interactions, cellular signaling pathways, transport reactions involving model barrier systems (e.g., cells or membrane fractions) for bioavailability screening, and a variety of other general systems. Cellular or organismal viability or activity may also be screened using the methods and apparatuses of the present invention, i.e., in toxicology studies.

In order to provide methods and devices for screening compounds for effects on biochemical systems, the present invention generally incorporates model in vitro systems which mimic a given biochemical system in vivo for which affector compounds are desired. The range of systems against which compounds can be screened and for which affector compounds are desired, is extensive. For example, compounds may be screened for effects in blocking, slowing or otherwise inhibiting key events associated with biochemical systems whose effect is undesirable. For example, test compounds may be screened for their ability to block systems that are responsible, at least in part, for the onset of disease or for the occurrence of particular symptoms of diseases, including, e.g., hereditary diseases, cancer, bacterial or viral infections and the like. Compounds which show promising results in these screening assay methods are then optionally subjected to further testing to identify effective pharmacological agents for the treatment of disease or symptoms of a disease. Alternatively, compounds can be screened for their ability to stimulate, enhance or otherwise induce biochemical systems whose function is believed to be desirable, e.g., to remedy existing deficiencies in a patient.

Once a model system is selected, batteries of test compounds are then applied against these model systems. By identifying those test compounds that have an effect on the particular biochemical system, in vitro, one can identify potential affectors of that system, in vivo.

In their simplest forms, the biochemical system models employed in the methods and apparatuses of the present invention will screen for an effect of a test compound on an interaction between two components of a biochemical system, e.g., receptor-ligand interaction, enzyme-substrate interaction, and the like. In this form, the biochemical system model will typically include the two normally interacting components of the system for which an affector is sought, e.g., the receptor and its ligand or the enzyme and its substrate.

Determining whether a test compound has an effect on this interaction then involves contacting the system with the test compound and assaying for the functioning of the system, e.g., receptor-ligand binding or substrate turnover. The assayed function is then compared to a control, e.g., the same reaction in the absence of the test compound or in the presence of a known affector.

Although described in terms of two-component biochemical systems, the methods and apparatuses may also be used to screen for affectors of much more complex systems where the result or end product of the system is known and assayable at some level, e.g., enzymatic pathways, cell signaling pathways and the like. Alternatively, the methods and apparatuses described herein may be used to screen for compounds that interact with a single component of a biochemical system, e.g., compounds that specifically bind to a particular biochemical compound, e.g., a receptor, ligand, enzyme, nucleic acid, structural macromolecule, etc.

Biochemical system models may also be embodied in whole cell systems. For example, where one is seeking to screen test compounds for an effect on a cellular response, whole cells may be utilized. Some general examples of cellular functions/responses that are of particular interest in pharmaceutical research include transport functions, i.e., ion channel activation, binding functions, i.e., ligand/receptor binding, nucleic acid hybridization, expression functions, i.e., gene expression and protein translocation, and overall cellular viability. Microfluidic cell-based screening assays for screening against these cellular functions are generally described in U.S. patent application Ser. No. 09/104,519, filed Jun. 25, 1998, which is incorporated herein by reference in its entirety for all purposes. Modified cell systems may also be employed in the screening systems encompassed herein. For example, chimeric reporter systems may be employed as indicators of an effect of a test compound on a particular biochemical system. Chimeric reporter systems typically incorporate a heterogenous reporter system integrated into a signaling pathway which signals the binding of a receptor to its ligand. For example, a receptor may be fused to a heterologous protein, e.g., an enzyme whose activity is readily assayable. Activation of the receptor by ligand binding then activates the heterologous protein which then allows for detection. Thus, the surrogate reporter system produces an event or signal which is readily detectable, thereby providing an assay for receptor/ligand binding. Examples of such chimeric reporter systems have been previously described in the art.

Additionally, where one is screening for bioavailability, e.g., transport, biological barriers may be included. The term "biological barriers" generally refers to cellular or membranous layers within biological systems, or synthetic models thereof. Examples of such biological barriers include the epithelial and endothelial layers, e.g. vascular endothelia and the like. In the case of cell-based screening operations therefore, a stream of a suspension of cells is transported along the main microfluidic channel to be contacted with the test compound plugs introduced therein.

Biological responses are often triggered and/or controlled by the binding of a receptor to its ligand. For example, interaction of growth factors, i.e., EGF, FGF, PDGF, etc., with their receptors stimulates a wide variety of biological responses including, e.g., cell proliferation and differentiation, activation of mediating enzymes, stimulation of messenger turnover, alterations in ion fluxes, activation of enzymes, changes in cell shape and the alteration in genetic expression levels. Accordingly, control of the interaction of the receptor and its ligand may offer control of the biological responses caused by that interaction.

Accordingly, in one aspect, the present invention is useful in screening for compounds that affect an interaction between a receptor molecule and its ligands. As used herein, the term "receptor" generally refers to one member of a pair of compounds, which specifically recognize and bind to each other. The other member of the pair is termed a "ligand." Thus, a receptor/ligand pair may include a typical protein receptor, usually membrane associated, and its natural ligand, e.g., another protein or small molecule. Receptor/ligand pairs may also include antibody/antigen binding pairs, complementary nucleic acids, nucleic acid associating proteins and their nucleic acid ligands. A large number of specifically associating biochemical compounds are well known in the art and can be utilized in practicing the present invention.

Traditionally, methods for screening for affectors of a receptor/ligand interaction have involved incubating a receptor/ligand binding pair in the presence of a test compound. The level of binding of the receptor/ligand pair is then compared to negative and/or positive controls. Where a decrease in normal binding is seen, the test compound is determined to be an inhibitor of the receptor/ligand binding. Where an increase in that binding is seen, the test compound is determined to be an enhancer or inducer of the interaction.

A similar, and perhaps overlapping, set of biochemical systems includes the interactions between enzymes and their substrates. The term "enzyme" as used herein, generally refers to a protein which acts as a catalyst to induce a chemical change in other compounds or "substrates."

Typically, affectors of an enzyme's activity toward its substrate are screened by contacting the enzyme with a substrate in the presence and absence of the compound to be screened and under conditions optimal for detecting changes in the enzyme's activity. After a set time for reaction, the mixture is assayed for the presence of reaction products or a decrease in the amount of substrate. The amount of substrate that has been catalyzed is then compared to a control, i.e., enzyme contacted with substrate in the absence of test compound or presence of a known effector. As above, a compound that reduces the enzymes activity toward its substrate is termed an "inhibitor," whereas a compound that accentuates that activity is termed an "inducer."

Generally, the various screening methods encompassed by the present invention involve the serial introduction of a plurality of test compounds into a microfluidic device. Once injected into the device, the test compound may be screened for effect on a biological system using a continuous serial or parallel assay orientation.

As used herein, the term "test compound" refers to the collection of compounds that are to be screened for their ability to affect a particular biochemical system. Test compounds may include a wide variety of different compounds, including chemical compounds, mixtures of chemical compounds, e.g., polysaccharides, small organic or inorganic molecules, biological macromolecules, e.g., peptides, proteins, nucleic acids, or an extract made from biological materials such as bacteria, plants, fungi, or animal cells or tissues, naturally occurring or synthetic compositions. Depending upon the particular embodiment being practiced, the test compounds may be provided, e.g., injected, free in solution, or may be attached to a carrier, or a solid support, e.g., beads. A number of suitable solid supports may be employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, glass beads, polyaminemethylvinylether maleic acid copolymer, amino acid copolymer, ethylene-maleic acid copolymer, nylon, silk, etc. Additionally, for the methods and apparatuses described herein, test compounds may be screened individually, or in groups. Group screening is particularly useful where hit rates for effective test compounds are expected to be low such that one would not expect more than one positive result for a given group.

In performing the screening assays described above, the functioning of the system is indicated by the production of a detectable event or signal. Typically, such detectable signals will include chromophoric or fluorescent signals that are associated with the functioning of the particular model biochemical system used. For enzyme systems, such signals will generally be produced by products of the enzyme's catalytic action, e.g., on a chromogenic or fluorogenic substrate. For binding systems, e.g., receptor ligand interactions, signals will typically involve the association of a labeled ligand with the receptor, or vice versa, or changes that the association imparts on the signal, quantitatively or temporally.

In preferred aspects, the continuous system generates a constant signal which varies only when a test compound is introduced that affects the system. Specifically, as the system components flow along the channel, they will produce a relatively constant signal level at a detection zone or window of the channel. Test compounds are periodically introduced into the channel and mixed with the system components. Where those test compounds have an effect on the system, it will cause a deviation from the constant signal level at the detection window. This deviation may then be correlated to the particular test compound screened.

For example, in those embodiments where the first component is an enzyme and the second a substrate, the substrate may be a chromogenic or fluorogenic substrate which produces an optically detectable signal when the enzyme acts upon the substrate. In the case where the first component is a receptor and the second is a ligand, either the ligand or the receptor may bear a detectable signal. In either event, the mixture and flow rate of compounds will typically remain constant such that the flow of the mixture of the first and second components past the detection window 116 will produce a steady-state signal. By "steady state signal" is generally meant a signal that has a regular, predictable signal intensity profile. As such, the steady-state signal may include signals having a constant signal intensity, or alternatively, a signal with a regular periodic intensity, against which variations in the normal signal profile may be measured. This latter signal may be generated in cases where fluid flow is periodically interrupted for, e.g., loading additional test compounds, as described in the description of the continuous flow systems. Although the signal produced in the above-described enzymatic system will vary along the length of the channel, i.e., increasing with time of exposure as the enzyme converts the fluorogenic substrate to the fluorescent product, the signal at any specific point along the channel will remain constant, given a constant flow rate.

For receptor/ligand systems, a similar variation in the steady state signal may also be observed. Specifically, the receptor and its fluorescent ligand can be made to have different flow rates along the channel. This can be accomplished by incorporating size exclusion matrices within the channel, or, in the case of electroosmotic methods, altering the relative electrophoretic mobility of the two compounds so that the receptor flows more rapidly down the channel. Again, this may be accomplished through the use of size exclusion matrices, or through the use of different surface charges in the channel which will result in differential flow rates of charge-varied compounds. Where a test compound binds to the receptor, it will result in a dark pulse in the fluorescent signal followed by a brighter pulse. Without being bound to a particular theory of operation, it is believed that the steady state signal is a result of both free fluorescent ligand, and fluorescent ligand bound to the receptor. The bound ligand is traveling at the same flow rate as the receptor while the unbound ligand is traveling more slowly. Where the test compound inhibits the receptor-ligand interaction, the receptor will not 'bring along' the fluorescent ligand, thereby diluting the fluorescent ligand in the direction of flow, and leaving an excess of free fluorescent ligand behind. This results in a temporary reduction in the steady-state signal, followed by a temporary increase in fluorescence. Alternatively, schemes similar to those employed for the enzymatic system may be employed, where there is a signal that reflects the interaction of the receptor with its ligand. For example, pH indicators which indicate pH effects of receptor-ligand binding may be incorporated into the device along with the biochemical system, i.e., in the form of encapsulated cells, whereby slight pH changes resulting from binding can be detected. See Weaver, et al., *Bio/Technology* (1988) 6:1084–1089. Additionally, one can monitor activation of enzymes resulting from receptor ligand binding, e.g., activation of kinases, or detect conformational changes in such enzymes upon activation, e.g., through incorporation of a fluorophore which is activated or quenched by the conformational change to the enzyme upon activation.

The present invention is further illustrated by the following nonlimiting examples.

EXAMPLES

The above-described calculations were used to determine optimal assay parameters for a microfluidic device that included an external sampling pipettor element ("capillary") with a rectangular reaction channel ("channel"), which utilized pressure driven flow to mix enzyme and substrate within the reaction channel while periodically introducing test compounds through the capillary element. A schematic illustration of the microfluidic device incorporating the external sampling capillary element is shown in FIGS. 3A and 3B. Table 2 (left column) illustrates the input values for the system, based upon the predetermined channel geometry and or assay requirements. Table 2 (right column) illustrates the optimized values for the remaining variables, once the predetermined or preordained values are ascertained.

| INPUT: | | CALCULATED: | |
|---|---|---|---|
| Channel Dimensions | | In Channel | |
| Width (a) | 74 | Max. velocity (cm/s) | 0.22 |
| Depth (b) | 12 | | |
| Reactor length (cm) | 3.2 | Avg. velocity (cm/s) | 0.13 |
| Main channel Length (cm) | 4.7 | Inhibitor E (cm$^2$/s) | $2.51 \times 10^{-4}$ |
| | | Substrate E (cm$^2$/s) | $7.53 \times 10^{-4}$ |
| Cross-section Area (cm$^2$) | $8.88 \times 10^{-6}$ | Enzyme E (cm$^2$/s) | $1.51 \times 10^{-3}$ |
| | | In capillary | |
| Aspect ratio (b/a) | 0.16 | Max Velocity (cm/s) | 0.72 |
| Ua/Um | 0.58 | Avg. velocity (cm/s) | 0.36 |
| f(b/a) | 6.7 | Inhibitor E (cm$^2$/s) | $9.1 \times 10^{-4}$ |
| Capillary Dimensions | | Substrate E (cm$^2$/s) | $2.7 \times 10^{-3}$ |
| Inner Diameter (μm) | 20 | Enzyme E (cm$^2$/s) | $5.5 \times 10^{-3}$ |
| Outer Diameter (μm) | 365 | Total time in cap. | 5.53 |
| Length (cm) | 2 | Dispersion (L) | |
| Area (cm$^2$) | $3.1 \times 10^{-6}$ | Inhib. in Cap. (cm) | 0.10 |
| Area ratio (chan./cap.) | 2.8 | Inhib. in Channel (cm) | 0.11 |
| Buffer/Analyte Prop. | | | |
| Inhibitor Diff. (cm$^2$/s) | $3 \times 10^{-6}$ | Subst. in Channel (cm) | 0.19 |
| Substrate Diff. (cm$^2$/s) | $1 \times 10^{-6}$ | | |
| Enzyme Diff. (cm$^2$/s) | $5 \times 10^{-7}$ | Enz. in Channel (cm) | 0.27 |
| Buffer Visc. (cP) | 1 | | |
| Incubation Time | | Limiting disp. (cm) | 0.27 |
| Time in Channel(s) | 25 | Init. plug L/disp. L (cm) (n) | 6.0 |
| Pressure Drop (psi) | 1.6 | | |
| | | Spacer length in chan. (cm) | 0.82 |

| INPUT: | CALCULATED: | |
|---|---|---|
| | Sample Length in chan. (cm) | 0.82 |
| | Spacer length in cap. (cm) | 2.33 |
| | Sample length in cap. (cm) | 2.33 |
| | Dwell time spacer(s) | 6.4 |
| | Dwell time sample(s) | 6.4 |
| | 1/throughput (s/sample) (P) | 12.9 |

As can be seen from Table 2, above, a number of assay and channel parameters were predetermined and/or preordained based upon the assay that was to be performed in the device to be performed, e.g., buffer/analyte properties and incubation time, as well as practicalities of the microfluidic device structure, e.g., channel and capillary dimensions. For example, incubation time is generally dictated by the kinetics of the assay that is to be performed. This, in turn, dictates the amount of time that a reaction mixture remains in the reaction channel, which is a function of flow rate and channel length. Similarly, channel depth can be dictated by the detection limits of the system used to detect signals within the channels, e.g., so as to permit the presence of adequate levels of signal at the detection zone.

Based upon these predetermined or preordained parameters, one can then determine other parameters that are optimized, e.g., for throughput and/or dispersion/diffusion. For example, in the example provided, the goal was to optimize the rate of throughput, which resulted in the calculation of values for flow velocities both in the channels of the device as well as within the external capillary element, as well as for the length of sample fluid plugs and spacer plugs, e.g., provided between sample fluid plugs, so as to permit optimal throughput without excessive intermixing of sample plugs, e.g., minimizing spacer plug length. By way of example, throughput is optimized by rearranging Equation (6) to yield:

$$P = n\left(d\sqrt{\frac{2KT}{D}} + \sqrt{\frac{2KT}{U}}\right) \quad (18)$$

Unless otherwise specifically noted, all concentration values provided herein refer to the concentration of a given component as that component was added to a mixture or solution independent of any conversion, dissociation, or reaction of that component to alter the component or transform that component into one or more different species once added to the mixture or solution. Further, although certain methods may be described or recited in the appended claims in a particular order of steps, it will be appreciated that the various steps can be practiced in any order unless an order of such steps is expressly provided in the language of the claims.

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

What is claimed is:

1. A method for performing a serial analysis in a microfluidic channel network, comprising:
   selecting a cycle length of a test plug containing a test compound plug and a spacer plug;
   identifying a diffusion coefficient of the test compound in the test compound plug;
   selecting a total reaction time for the test compound;
   determining one or more of a maximum channel cross-sectional dimension and a channel length for carrying out the analysis, based upon the cycle length, diffusion coefficient and total reaction time, whereby the test compound in the test compound plug disperses a distance that is less than 200% of the test compound plug length during the total reaction time;
   providing at least a first microfluidic channel that comprises one or more of the maximum channel cross-sectional dimension and channel length;
   introducing at least a first test plug having the cycle length into the at least first microfluidic channel; and
   analyzing the test compound in the first microfluidic channel.

2. The method of claim 1, wherein the test compound plug disperses a distance that is less than 100% of the test compound plug length during the total reaction time.

3. The method of claim 1, wherein the test compound plug disperses a distance that is less than 50% of the test compound plug length during the total reaction time.

4. The method of claim 1, wherein the test compound plug disperses a distance that is less than 25% of the test compound plug length during the total reaction time.

5. The method of claim 1, wherein the first microfluidic channel comprises a circular cross-section, and the cross-sectional dimension is a diameter of the first microfluidic channel.

6. The method of claim 1, wherein the first microfluidic channel comprises a rectangular cross-section, and the cross-sectional dimension is a depth of the first microfluidic channel.

7. The method of claim 1, wherein the first microfluidic channel comprises an elliptical cross-section, and the cross-sectional dimension is a minor axis of the first microfluidic channel.

8. The method of claim 1, wherein the test plug length is from about 0.1 to about 30 mm.

9. The method of claim 1, wherein the test plug length is from about 1 to about 10 mm.

10. The method of claim 1, comprising introducing at least a second test plug having the cycle length into the first microfluidic channel and analyzing the second test plug in the first microfluidic channel.

11. The method of claim 1, wherein the at least first channel is disposed in a planar microfluidic device.

12. The method of claim 11, wherein the planar microfluidic device comprises at least a second microfluidic channel disposed therein.

13. The method of claim 12, wherein the second microfluidic channel is in fluid communication with the first microfluidic channel.

14. The method of claim 11, wherein the planar microfluidic device comprises an integrated pipettor element extending from the planar microfluidic device, the pipettor element having a capillary channel disposed therethrough, wherein the capillary channel in the pipettor element is in fluid communication with the first microfluidic channel.

15. The method of claim 14, wherein the first test plug is drawn into the first microfluidic channel through the capillary channel in the pipettor element.

* * * * *